US00PP15539P2

(12) United States Plant Patent
Misato et al.

(10) Patent No.: US PP15,539 P2
(45) Date of Patent: Feb. 8, 2005

(54) ***MANDEVILLA* PLANT NAMED 'SUNMANDECRIM'**

(50) Latin Name: ***Mandevilla atroviolacea*×(*Mandevilla amabalis*×*boliviensis*)**
Varietal Denomination: Sunmandecrim

(75) Inventors: Tomoya Misato, Omihachiman (JP); Yasuyuki Murakami, Gamo-gun (JP)

(73) Assignee: Suntory Flowers Limted, Tokyo (JP)

( * ) Notice: Subject to any disclaimer, the term of this patent is extended or adjusted under 35 U.S.C. 154(b) by 0 days.

(21) Appl. No.: 10/692,275

(22) Filed: Oct. 22, 2003

(51) Int. Cl.[7] ..... A01H 5/00
(52) U.S. Cl. ..... Plt./232
(58) Field of Search ..... Plt./232

(56) References Cited
U.S. PATENT DOCUMENTS

PP11,556 P 10/2000 Tachibana et al.

*Primary Examiner*—Kent Bell
(74) *Attorney, Agent, or Firm*—Christie, Parker and Hale, LLP

(57) ABSTRACT

A new and distinct variety of *Mandevilla* plant is provided that was created through controlled cross-breeding. The female parent is a seedling of *Mandevilla atroviolacea* and the male parent is a *Mandevilla amabilis*×*boliviensis* 'Sunmandeho' plant. The new variety exhibits a lianous growth habit and well tolerates heat. Attractive deep red flowers having a brilliant orange inside throat are formed over an extended period of time. The flower petals curve outwards. Moderate olive green leaves having smooth surface and an entire margin are formed. The leaf surface is smooth. Plants of the new variety are well suited for growing in pots that are equipped with a support for climbing.

2 Drawing Sheets

Botanical classification: *Mandevilla atroviolacea*×(*Mandevilla amabalis*×*boliviensis*).
Variety denomination: 'Sunmandecrim'.

BACKGROUND OF THE VARIETY

The present invention relates to a new and distinct variety of *Mandevilla* plant obtained from crossing a seedling of an unnamed *Mandevilla atroviolacea* plant (female) and a *Mandevilla amabilis*×*boliviensis* 'Sunmandeho' plant (male).

The *Mandevilla* is a popular plant and is used as a pot plant in the summer season or an indoor plant or a glasshouse plant. Only a limited number of varieties of *Mandevilla* plants are commercially available. Accordingly, this invention was aimed at obtaining a new variety having a large flower with deep red petals, and a long flowering duration.

In September 1997, crossing with a seedling of *Mandevilla atroviolacea* and *Mandevilla* plant 'Sunmandeho' (U.S. Plant Pat. No. 11,556) was conducted. From that crossing, 40 seedlings were obtained. Those seedlings were grown in a greenhouse from April 1998, and only one seedling was selected in August 1999. The selected plant was propagated by cutting and then grown in bed and pot on trial from August 1999 to November 2000. The botanical characteristics of the plant were examined, using similar variety 'Sunmandeho' and 'Rose Giant' (non-patented in the United States), for comparison. As a result, it was concluded that this new *Mandevilla* plant is distinguishable from any other variety, whose existence is known to us, and is uniform and stable in its characteristics. This new variety of *Mandevilla* plant was named 'Sunmandecrim'. The new variety reproduces true to type in successive generations of asexual reproduction.

In the following description, the color-coding is in accordance with the R.H.S. Colour Chart of The Royal Horticultural Society, London, England.

The female parent in the obtaining of this new variety 'Sunmandecrim' is a seedling of *Mandevilla atroviolacea* (non-patented in the United States). The *Mandevilla* plant *Mandevilla atroviolacea* also is presently maintained at Yokaichi-shi, Shiga, Japan. The main botanical characteristics of *Mandevilla atroviolacea* are as follows:

Plant:
- *Growth habit.*—Lianous.

Stem:
- *Stem diameter.*—Approximately 2.1 mm.
- *Stem color.*—Light brown (R.H.S. Colour Chart No. 166D).
- *Lenticel.*—Present.
- *Branching.*—Few.
- *Internode length.*—Approximately 3.8 cm.

Leaf:
- *Phyllotaxis.*—Opposite.
- *Whole shape of leaf.*—Oblong.
- *Shape of leaf apex.*—Cuspidate.
- *Shape of leaf base.*—Cordate.
- *Leaf length.*—Approximately 5.0 cm.
- *Leaf width.*—Approximately 2.5 cm.
- *Leaf thickness.*—Approximately 0.2 mm.
- *Color of mature leaf upper side.*—Dark olive green (R.H.S. Colour Chart No. 137A).
- *Color of mature leaf reverse side.*—Moderate yellow green (R.H.S. Colour Chart No. 147B).
- *Variegation of mature leaf.*—Absent.
- *Gloss of mature leaf upper side.*—Medium.
- *Pubescence of mature leaf upper side.*—Absent.
- *Pubescence of mature leaf reverse side.*—Absent.
- *Leaf petiole length.*—Approximately 1.0 cm.
- *Leaf petiole diameter.*—Approximately 1.5 mm.
- *Leaf petiole color.*—Moderate yellow green (R.H.S. Colour Chart No. 146C).

Flower:
*Color of flower bud.*—Strong purplish pink (R.H.S. Colour Chart No. 55B).
*Length of peduncle.*—Approximately 3.0 cm.
*Peduncle color.*—Dark reddish orange (R.H.S. Colour Chart No. 178A).
*Flower shape.*—Single.
*Flower form.*—Partly open.
*Flower facing direction.*—Horizontal to slanted upward.
*Diameter of flower.*—Approximately 5.5 cm.
*Flower height.*—Approximately 6.5 cm.
*Floral tube length.*—Approximately 5.5 cm.
*Color of flower upper side.*—Moderate purplish-red (R.H.S. Colour Chart No. 64B).
*Color of inside surface of corolla throat.*—Vivid orange (R.H.S. Colour Chart No. 24A).
*Color of flower outside.*—Strong purplish pink (R.H.S. Colour Chart No. 55B).
*Overlapping of petals.*—Slightly overlapped.
*Whole shape of petal lobe.*—Orbicular.
*Shape of petal lobe apex.*—Cuspidate.
*Curvature of petal.*—Inwardly curved.
*Waving of petal.*—Weak.
*Petal length.*—Approximately 2.0 cm.
*Petal width.*—Approximately 2.1 cm.
*Petal number.*—5.
Reproductive organs:
*Pistil.*—Present.
*Pistil number.*—1.
*Stamen number.*—5.
*Anther color.*—Dark reddish orange (R.H.S. Colour Chart No. 178A).
*Anther appendage.*—Absent.
Physiological and ecological characteristics:
*Flower number.*—5–9 per cluster.
*Flower fragrance.*—Absent.
*Fertility.*—Absent.
*Leaf abscission.*—The leaves fall when subjected to low temperature in late autumn.
*Flower abscission.*—The flowers commonly last approximately 7 to 10 days on the plant.
*Flowering time.*—Early.
*Flowering duration.*—Long (early June to late October in Japan).
*Cold tolerance.*—Low.
*Heat tolerance.*—High.
*Resistance to diseases.*—Medium.
*Resistance to pests.*—Medium.

The *Mandevilla amabilis×boliviensis* 'Sunmandeho' used as the male parent in the obtaining of this new variety 'Sunmandecrim' is commercially available. The *Mandevilla amabilis×boliviensis* 'Sunmandeho' also is presently maintained at the SUNTORY FLOWERS Ltd., at 863-1, Aza-Iketani, Omori-cho, Yokaichi, Shiga, Japan. The main botanical characteristics of *Mandevilla amabilis×boliviensis* 'Sunmandeho' are as follows:

Plant:
*Growth habit.*—Lianous.
Stem:
*Stem diameter.*—Approximately 4.5 mm.
*Stem color.*—Moderate Orange (R.H.S. Colour Chart No. 167D).
*Lenticel.*—Not visible.
*Branching.*—Few.
*Internode length.*—Approximately 13.0 cm.
Leaf:
*Phyllotaxis.*—Opposite.
*Whole shape of leaf.*—Elliptic.
*Shape of leaf apex.*—Cuspidate.
*Shape of leaf base.*—Acute.
*Leaf length.*—Approximately 11.0 cm.
*Leaf width.*—Approximately 5.0 cm.
*Leaf thickness.*—Approximately 0.2 mm.
*Leaf margin.*—Entire.
*Color of mature leaf upper side.*—Medium olive green (R.H.S. Colour Chart No. 146A).
*Color of mature leaf reverse side.*—Medium yellow green (R.H.S. Colour Chart No. 146C).
*Variegation of mature leaf.*—Absent.
*Gloss of mature leaf upper side.*—Medium-strong.
*Pubescence of mature leaf upper side.*—Absent.
*Pubescence of mature leaf reverse side.*—Absent.
*Leaf petiole length.*—Approximately 1.5 cm.
*Leaf petiole diameter.*—Approximately 2.2 mm.
*Leaf petiole color.*—Brilliant yellow green (R.H.S. Colour Chart No. 145B).
Flower:
*Color of flower bud.*—Light yellow green (R.H.S. Colour Chart No. 149C).
*Length of peduncle.*—Approximately 1.6 cm.
*Peduncle color.*—Strong yellow green (R.H.S. Colour Chart No. 144B).
*Flower shape.*—Single.
*Flower form.*—Perfectly open.
*Flower facing direction.*—Horizontal to slanted upward.
*Diameter of flower.*—Approximately 11.0 cm.
*Flower height.*—Approximately 9.0 cm.
*Floral tube length.*—Approximately 5.5 cm.
*Color of flower upper side.*—Yellowish white (R.H.S. Colour Chart No. 155C).
*Color of inside surface of corolla throat.*—Vivid yellow (R.H.S. Colour Chart No. 15A).
*Color of flower outside.*—Yellowish white (R.H.S. Colour Chart No. 158D).
*Overlapping of petals.*—Slightly overlapped.
*Whole shape of petal lobe.*—Orbicular.
*Shape of petal lobe apex.*—Cuspidate.
*Curvature of petal.*—Outwardly curved.
*Waving of petal.*—Medium.
*Petal length.*—Approximately 5.5 cm.
*Petal width.*—Approximately 6.0 cm.
*Petal number.*—5.
Reproductive organs:
*Pistil.*—Present.
*Pistil number.*—1.
*Stamen number.*—5.
*Anther color.*—Brilliant yellow (R.H.S. Colour Chart No. 15B).
*Anther appendage.*—Absent.
Physiological and ecological characteristics:
*Flower number.*—Commonly 4–5 per cluster.
*Flower fragrance.*—Absent or weak.
*Fertility.*—Self fertile.
*Leaf abscission.*—The leaves fall when subjected to low temperature in late autumn.
*Flower abscission.*—The flowers commonly last approximately 7 to 10 days on the plant.

*Flowering duration.*—Long and substantially continuous (early June to early November in Japan).
*Cold tolerance.*—Low.
*Heat tolerance.*—High.
*Resistance to diseases.*—Medium.
*Resistance to pests.*—Medium.

The similar variety *Mandevilla amabilis* 'Rose Giant' is commercially available. The *Mandevilla* plant *Mandevilla amabilis* 'Rose Giant' also is presently maintained at the SUNTORY FLOWERS Ltd., at 836-1, Aza-Iketani, Omori-cho, Yokaichi, Shiga, Japan. The main botanical characteristics of *Mandevilla amabilis* 'Rose Giant' are as follows:

Plant:
*Growth habit.*—Lianous.
Stem:
*Stem diameter.*—Approximately 6.0 mm.
*Stem color.*—Dark reddish brown (R.H.S. Colour Chart No. 183A).
*Lenticel.*—Present.
*Branching.*—Few.
*Internode length.*—Approximately 17.0 cm.
Leaf:
*Phyllotaxis.*—Opposite.
*Whole shape of leaf.*—Oblong.
*Shape of leaf apex.*—Mucronate.
*Shape of leaf base.*—Cordate.
*Leaf length.*—Approximately 11.0 cm.
*Leaf width.*—Approximately 7.0 cm.
*Leaf thickness.*—Approximately 0.4 mm.
*Color of mature leaf upper side.*—Dark grayish olive green (R.H.S. Colour Chart No. 139A).
*Color of mature leaf reverse side.*—Moderate yellow green (R.H.S. Colour Chart No. 147B).
*Varieagation of mature leaf.*—Absent.
*Gloss of mature leaf upper side.*—Medium.
*Pubescence of mature leaf upper side.*—Present.
*Pubescence of mature leaf reverse side.*—Present.
*Leaf petiole length.*—Approximately 1.0 cm.
*Leaf petiole diameter.*—Approximately 3.5 mm.
*Leaf petiole color.*—Brilliant yellow green (R.H.S. Colour Chart No. 149B).
Flower:
*Color of flower bud.*—Strong purplish pink (R.H.S. Colour Chart No. 62B).
*Length of peduncle.*—Approximately 0.9 cm.
*Peduncle color.*—Vivid yellow green (R.H.S. Colour Chart No. 149A).
*Flower shape.*—Single.
*Flower form.*—Perfectly open.
*Flower facing direction.*—Horizontal to slanted upward.
*Diameter of flower.*—Approximately 10.0 cm.
*Flower height.*—Approximately 9.0 cm.
*Floral tube length.*—Approximately 5.5 cm.
*Color of flower upper side.*—Deep purplish pink (R.H.S. Colour Chart No. 55A).
*Color of inside surface of corolla throat.*—Yellowish white (R.H.S. Colour Chart No. 155D).
*Color of flower outside.*—Deep purplish pink (R.H.S. Colour Chart No. 55A).
*Overlapping of petals.*—Closed.
*Whole shape of petal lobe.*—Orbicular.
*Shape of petal lobe apex.*—Cuspidate.
*Curvature of petal.*—Outwardly curved.
*Waving of petal.*—Weak.
*Petal length.*—Approximately 5.5 cm.
*Petal width.*—Approximately 6.0 cm.
*Petal number.*—5.
Reproductive organs:
*Pistil.*—Present.
*Pistil number.*—1.
*Stamen number.*—5.
*Anther color.*—Bright yellow (R.H.S. Colour Chart No. 15B).
*Anther appendage.*—Absent.
Physiological and ecological characteristics:
*Flower number.*—5–9 per cluster.
*Flower fragrance.*—Absent-weak.
*Fertility.*—Absent.
*Leaf abscission.*—The leaves fall when subjected to low temperature in late autumn.
*Flower abscission.*—The flowers commonly last approximately 7 to 10 days on the plant.
*Flowering time.*—Early.
*Flowering duration.*—Long (early June to late October in Japan).
*Cold tolerance.*—Low.
*Heat tolerance.*—High.
*Resistance to diseases.*—Medium.
*Resistance to pests.*—Medium.

This new variety of *Mandevilla* plant 'Sunmandecrim' was asexually reproduced by cuttings at Yokaichi-shi, Shiga, Japan and the homogeneity and stability thereof were thereby confirmed.

SUMMARY OF THE NEW VARIETY

This new variety of *Mandevilla* plant possesses a lianous growth habit. The blooming period is from early June to early November in Japan and the flowering duration is long. When growing conditions are above 18° C., flowering is substantially continuous. The flower diameter is large. Both surfaces of the petals are deep red (R.H.S. Colour Chart No. 45A) and the inside surface of corolla throat is brilliant orange. The leaves are moderate olive green and are hairless on both faces. The plant is highly tolerant to heat.

BRIEF DESCRIPTION OF THE PHOTOGRAPHS

DETAILED DESCRIPTION OF THE NEW VARIETY

Figure 1:
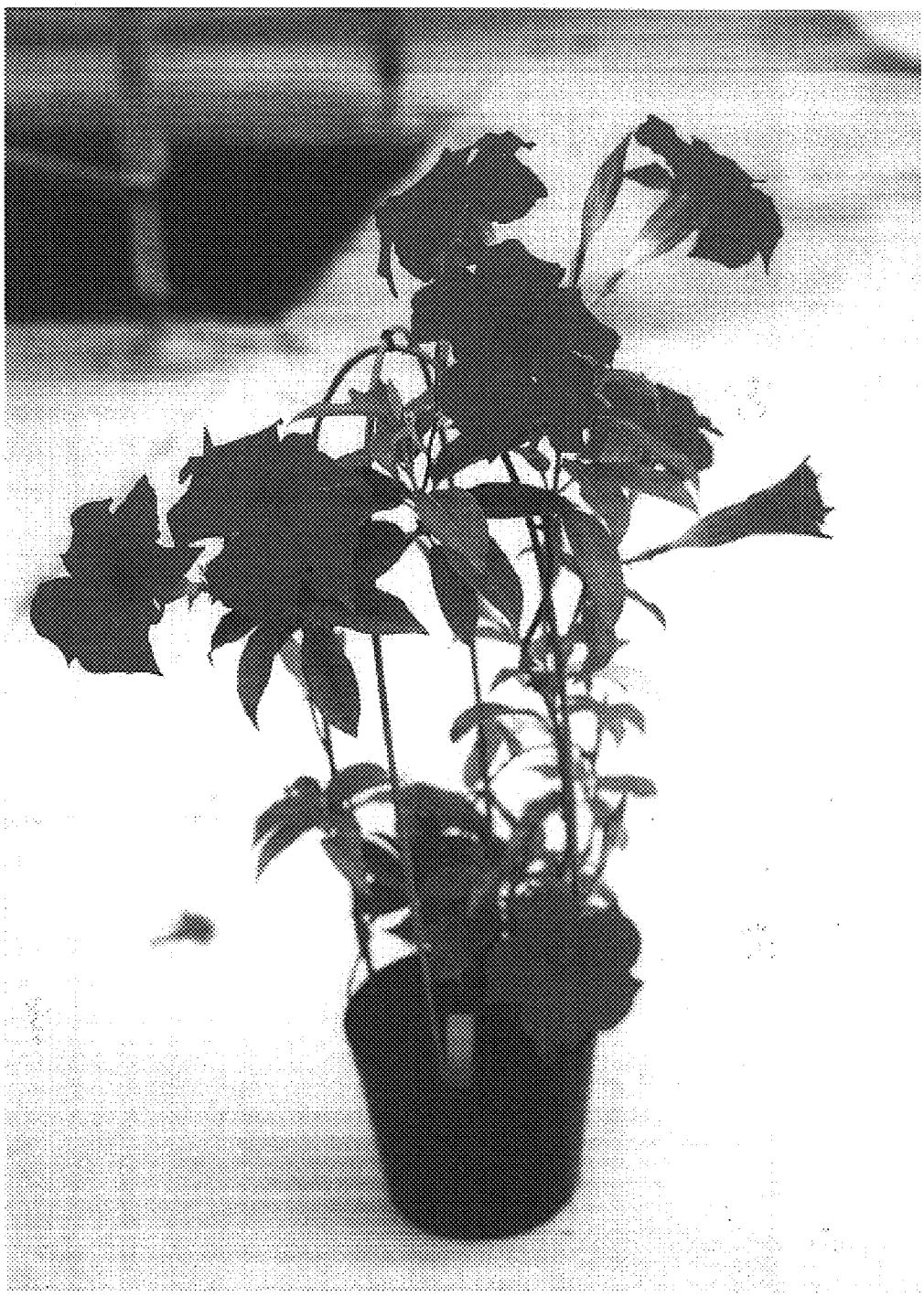
FIG. 1 is photograph of the new 'Sunmandecrim' variety of *Mandevilla* plant when growing in a pot.
Figure 2:
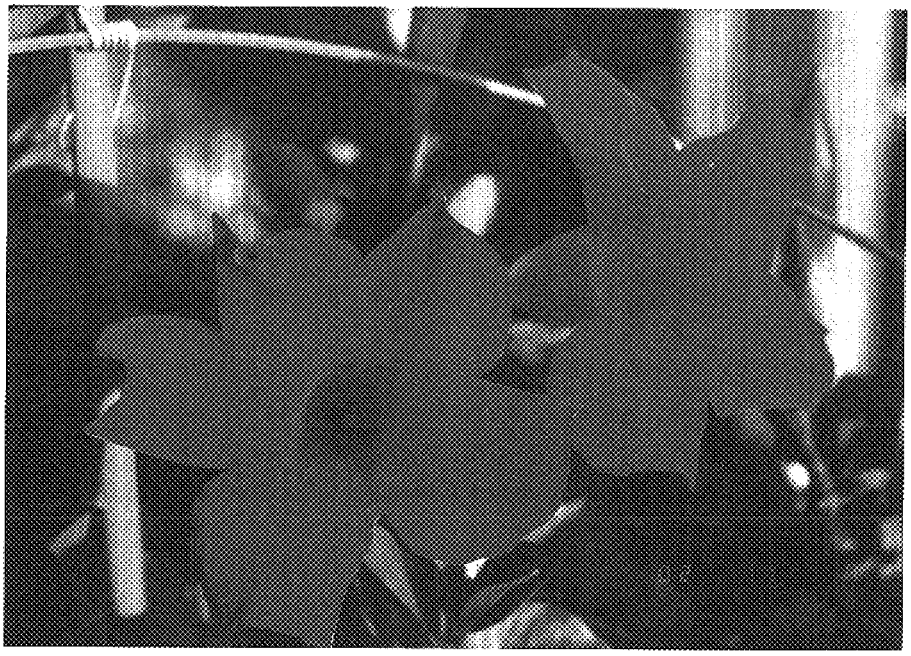
FIG. 2 is close up photograph of flowers of the new 'Sunmandecrim' variety of *Mandevilla* plant.

The plant as described was grown in a 30 cm diameter pot at a greenhouse in Yokaichi-shi, Shiga-ken, Japan. The age of the plant as described is approximately eight months. The botanical characteristics of the new 'Sunmandecrim' variety of *Mandevilla* plant are as follows:

Plant:
*Growth habit.*—Lianous.
*Growth height* (*length*).—Approximately 2.5 m. Requires a support to keep upright growth, as it is a twining plant.
*Growth width.*—Approximately 37 cm.
Stem:
*Stem diameter.*—Approximately 2.8 mm.
*Stem length.*—Approximately 2.5 m.

*Stem color.*—Dark orange yellow (R.H.S. Colour Chart No. 163A).
*Lenticel.*—Not visible.
*Branching.*—Few.
*Internode length.*—Approximately 5.5 cm.

Leaf:
*Phyllotaxis.*—Opposite.
*Whole shape of leaf.*—Oblong.
*Shape of leaf apex.*—Mucronate.
*Shape of leaf base.*—Cordate.
*Leaf length.*—Approximately 5.5 cm.
*Leaf width.*—Approximately 3.8. cm.
*Leaf thickness.*—Approximately 0.2 mm.
*Leaf margin.*—Entire.
*Color of mature leaf upper side.*—Moderate olive green (R.H.S. Colour Chart No. 144B).
*Color of mature leaf reverse side.*—Moderate yellow green (R.H.S. Colour Chart No. 144B).
*Variegation of mature leaf.*—Absent.
*Gloss of mature leaf upper side.*—Medium-strong.
*Pubescence of mature leaf upper side.*—Absent.
*Pubescence of mature leaf reverse side.*—Absent.
*Leaf petiole length.*—Approximately 1.1 cm.
*Leaf petiole diameter.*—Approximately 1.5 mm.
*Leaf petiole color.*—Strong yellow green (R.H.S. Colour Chart No. 144A).

Flower:
*Color of flower bud.*—Deep red (R.H.S. Colour Chart No. 45D).
*Length of bud.*—Approximately 8 cm.
*Diameter of bud.*—Approximately 1.5 cm.
*Shape of bud.*—Fusiform.
*Length of peduncle.*—Approximately 0.6 cm.
*Width of peduncle.*—Approximately 2.0 mm.
*Peduncle color.*—Moderate yellow green (R.H.S. Colour Chart No. 146D).
*Flower shape.*—Flared trumpet, corolla fused, five-parted; petals overlapping.
*Flower form.*—Perfectly open.
*Flower facing direction.*—Horizontal to slanted upward.
*Diameter of flower.*—Approximately 8.0 cm.
*Flower height.*—Approximately 5.5 cm.
*Floral tube length.*—Approximately 3.5 cm.
*Floral tube diameter is.*—Approximately 1.8 cm.
*Color of flower upper side.*—Deep red (R.H.S. Colour Chart No. 45A).
*Color of inside surface of corolla throat.*—Brilliant orange (R.H.S. Colour Chart No. 30A).
*Color of flower under side.*—Vivid red (R.H.S. Colour Chart No. 46B).
*Whole shape of petal lobe.*—Ovate.
*Shape of petal lobe apex.*—Cuspidate.
*Curvature of petal.*—Outwardly curved.
*Petal margin.*—Entire.
*Petal length.*—Approximately 3.8 cm.
*Petal width.*—Approximately 3.2 cm.
*Petal number.*—5.
*Number of sepals.*—5.
*Sepal length.*—Approximately 6.0 mm.
*Sepal width.*—Approximately 1.0 mm.
*Sepal color.*—Near 145B (both sides).

Reproductive organs:
*Pistil.*—Present.
*Pistil number.*—1.
*Stamen number.*—5.
*Anther color.*—Light yellow (R.H.S. Color Chart No. 14C).
*Anther appendage.*—Absent.
*Seed.*—Approximately 200 per fruit; seed length approximately 5.0 mm; seed width approximately 1.5 mm. The seed has coma. The coloration R.H.S. near 145A.
*Pedicel.*—Length approximately 2.5 cm; diameter 2.0 cm; coloration near 146D.

Physiological and ecological characteristics:
*Flower number.*—Commonly 9 per cluster.
*Flower fragrance.*—Absent or weak.
*Fertility.*—Self fertile.
*Leaf abscission.*—The leaves fall when subjected to low temperature in late autumn.
*Flower abscission.*—The flowers commonly last approximately 7 to 10 days on the plant.
*Flowering time.*—Medium.
*Flowering duration.*—Long and substantially continuous (early June to early November in Japan).
*Tolerance.*—The hardiness of the instant variety is 11 by USDA Hardiness Zone. The plant grows well at temperatures up to at least 30° C.; the lowest and upper temperature for plant survival has not been evaluated.

Resistance to diseases and pests: A slight degree of damage has been observed and no serious damage by white fly, aphids has been observed. No diseases have been observed.

This new variety of *Mandevilla* plant, 'Sunmandecrim' is most suitable for potting in the summer season or for use as an indoor plant or as a glasshouse plant. This new variety exhibits a lianous growth habit and can be readily trained to grow on a wire or other upright support.

We claim:

1. A new and distinct variety of *Mandevilla* plant named 'Sunmandecrim' substantially as herein illustrated and described.

* * * * *